United States Patent
Navarro et al.

(10) Patent No.: US 6,939,357 B2
(45) Date of Patent: Sep. 6, 2005

(54) INSTRUMENT FOR CLOSING, BY SUBCUTANEOUS SUTURING, AN ORIFICE MADE IN THE ABDOMINAL WALL OF A PATIENT

(76) Inventors: Francis Navarro, 56 rue de Montaury, 30900 Nimes (FR); Jacques Domergue, 65 Avenue du Muscadet, 34000 Montpellier (FR)

( * ) Notice: Subject to any disclaimer, the term of this patent is extended or adjusted under 35 U.S.C. 154(b) by 317 days.

(21) Appl. No.: 10/137,203

(22) Filed: May 1, 2002

(65) Prior Publication Data

US 2003/0028201 A1 Feb. 6, 2003

(30) Foreign Application Priority Data

May 4, 2001 (FR) .......................................... 01 06022

(51) Int. Cl.⁷ .............................................. A61B 17/04
(52) U.S. Cl. ........................ 606/145; 606/144; 606/213
(58) Field of Search ................................ 606/144, 145, 606/213

(56) References Cited

U.S. PATENT DOCUMENTS

| | | | |
|---|---|---|---|
| 5,320,632 A | * | 6/1994 | Heidmueller ............... 606/144 |
| 5,374,275 A | | 12/1994 | Bradley et al. ............. 606/144 |
| 5,470,338 A | * | 11/1995 | Whitfield et al. ........... 606/144 |
| 5,527,321 A | * | 6/1996 | Hinchliffe .................... 606/144 |
| 5,741,279 A | | 4/1998 | Gordon et al. .............. 606/144 |
| 5,836,955 A | * | 11/1998 | Buelna et al. ............... 606/148 |
| 5,860,990 A | * | 1/1999 | Nobles et al. .............. 606/144 |
| 5,860,991 A | | 1/1999 | Klein et al. .................. 606/144 |
| 6,117,144 A | * | 9/2000 | Nobles et al. .............. 606/144 |
| 6,136,010 A | * | 10/2000 | Modesitt et al. ............ 606/144 |
| 6,245,079 B1 | * | 6/2001 | Nobles et al. .............. 606/144 |

* cited by examiner

*Primary Examiner*—Gary Jackson
(74) *Attorney, Agent, or Firm*—Ladas & Parry LLP

(57) ABSTRACT

An instrument for closing, by subcutaneous suturing, an orifice made in the abdominal wall of a patient. The instrument has a piston rod (5) whose end acts on a flexible support strip (8) for needles (7), thus causing them to emerge at an exterior of the lower part (4) of a cannula (3) of the instrument underneath the abdominal wall (2), so that the needle can then penetrate into a thick part of this wall. Also, a method for suturing of orifices after a surgical operation by laparoscopy.

15 Claims, 9 Drawing Sheets

INSTRUMENT FOR CLOSING, BY SUBCUTANEOUS SUTURING, AN ORIFICE MADE IN THE ABDOMINAL WALL OF A PATIENT

FIELD OF INVENTION

The present invention relates to an instrument for closing, by subcutaneous suturing, an orifice made in the abdominal wall of a patient.

It also relates to a procedure for closing such an orifice by subcutaneous suturing.

BACKGROUND OF THE INVENTION

When a surgical operation is performed by laparoscopy, the patient's abdomen is inflated by a gas and the surgeon uses trocars for the surgical procedure.

A trocar is a cylindrical device that passes through the abdominal wall of the patient and through which the instrument or instruments for performing the surgical operation are passed.

To position these cylindrical trocars, which can have a diameter of 5 to 15 mm, it is necessary to make an incision in the skin and the trocar is inserted into the abdomen with its pointed end, which is provided with protective means. On completion of the surgical operation, the trocar is withdrawn and the orifice through which it was introduced, having a length of about 12 mm, must be closed once again to allow proper healing. If the orifices for passage of trocars are longer than 10 mm, they must be closed by suturing the subcutaneous layers, or in other words the aponeurosis and the muscle, which is the resistant rigid part. Heretofore such orifices were closed by placing a suture stitch at the level of the superficial or deep aponeurosis depending on the thickness of the abdominal walls of the patients. The major difficulty in placing such a suture stitch is in spreading the skin, which is the most superficial part, and then locating the muscle and aponeurosis layer, which is the most rigid tissue, where the suture stitch must be placed and knotted from outside to inside. Surgeons often have difficulties in closing the deep tissue that is the aponeurosis, and in some cases this tissue is not reclosed. In addition, certain complications can develop, such as failure of the deep orifice to heal and to close, leading to evisceration. Another possible complication is strangulation of intraabdominal elements such as the small intestine within this orifice, with the risk of causing intestinal occlusions or other digestive complications.

SUMMARY OF INVENTION

The object of the present invention is to overcome the foregoing problems by providing an instrument with which an orifice made in the abdominal wall of a patient can be closed efficiently to allow proper healing of this orifice.

To this end, the inventive instrument with which there can be closed, by subcutaneous suturing, an orifice made in the abdominal wall of a patient for passage of a trocar that has been used for a surgical operation by laparoscopy, is characterized in that it comprises a cylindrical rigid cannula, one end part of which can be introduced into the orifice; a piston extending coaxially in the cannula and being operable externally by an operator; two needles movably attached to the diametrically opposite ends of a support member, which itself is supported in the end part of the cannula and which can occupy, under the action of the piston, a collapsed position in which the needles are drawn back into the end part of the cannula and an extended position after introduction of the cannula into the orifice, in which the needles project completely out of the cannula underneath the abdominal wall by passing through respectively two longitudinal slots of the lateral wall of the cannula, and are inclined relative to the longitudinal axis of the cannula on both sides thereof and are directed toward one another; a means for extracting the needles, which is mounted slidingly in the cannula, concentrically with the piston, and which can be maneuvered by the operator so that it can be displaced from a low position in the end part of the cannula to a high position in the upper end part thereof in such a way that, during this displacement, it simultaneously catches the two needles, which were introduced beforehand into the abdominal wall and which penetrate obliquely toward one another in the orifice and the cannula through longitudinal slots, and extracts them from the support member in order to guide them into the cannula, at the same time pulling a suture thread into the abdominal wall and the cannula, the thread having its ends integral respectively with the two needles and defining a loop, which is situated outside the cannula and which passes through the orifice to the outside of the abdominal wall, the ends of the thread then being accessible, so that they can be grasped and cut by the operator after complete retraction of the cannula from the orifice, in order to close the said orifice by tying a knot with the two strands of the thread.

Preferably the piston is a central rigid rod, which is guided slidingly in the extraction means and whose lower end is connected to the support member of the needles and whose upper end part passes through an upper transverse sealing wall of the cannula, the rod being designed to be retained axially in the cannula by a manually releasable locking means in such a way as to exert on the support member an axial force for retracting the needles in the cannula to permit introduction thereof into the orifice, after which the operator can release the locking means to displace the rod in a direction that causes extension of the support member and emergence of the needles from the cannula.

The extraction means comprises a sliding cylindrical upper part in the cannula, a cylindrical lower end part of smaller diameter, in which there is slidingly mounted the lower end part of the rod, and an intermediate linking part constituted in particular by two oblique walls, which converge toward the lower end part and each of which comprises a longitudinal slot that permits, when the extraction means is in low position, passage of the corresponding needle to its emerged position, in which it projects out of the cannula, each slot being terminated above the lower part of the extraction means by two V-shaped rims, in which the hook-shaped end of the needle can be caught during the displacement of the extraction means toward the upper part of the cannula.

The extraction means further comprises two diametrically opposite external gripping tabs, which are integral with the upper part of this means and project radially through respectively two longitudinal slots in the lateral wall of the cannula situated above the slots for passage of the needles, a precompressed spring being mounted between the extraction means and the cannula to return the extraction means to its low position.

The needles are curved and situated respectively in two planes parallel to the longitudinal central plane of the cannula, disposed on both sides of this central plane at equal distances therefrom in such a way as to allow the needles to occupy their drawn-in position in which they cross in the lower part of the cannula.

The needles are mounted movably via their ends at positions opposite to the hook-shaped ends respectively in two bases, which have circular, triangular or other cross section and are integral with the ends of the support member, the axis of each base being inclined relative to the corresponding end support plane of the support member to facilitate extraction of the needles during the upward movement of the extraction means in the cannula.

Once the needles have emerged from the cannula to occupy their position underneath the abdominal wall, they are introduced into the wall by pulling on the cannula to make them penetrate into the wall, and then exerting a force on the piston in a direction corresponding to retraction of the needles toward the cannula, whereupon the ends of the needles penetrate into the orifice and into the cannula through the two diametrically opposite slots thereof.

The two planes containing respectively the two needles are situated on both sides of the piston rod.

According to one embodiment, the support member is constituted by a flexible strip which at its ends carries the two needles and is maintained in the lower part of the cannula, such that it is perpendicular to the longitudinal middle plane thereof, by two pairs of support pins parallel to the strip, disposed on both sides of the transverse central plane of the strip, symmetrically with respect thereto, and integral with the body of the cannula, being perpendicular to its longitudinal central plane, the two pins of each pair being situated on each side of the strip in immediate proximity thereto in order to modify, by bending, the radius of curvature of the strip by sliding it between the support pins under the action of the piston rod, whose lower end is integral with the geometric center of the strip, and in order to displace toward this center toward the top or toward the bottom of the cannula, so that the needles emerge from or are drawn back into the cannula, and ultimately are drawn partly back into the cannula.

According to another embodiment, the support member is constituted by two arms mounted pivotally on a common central pin integral with the body of the cannula in the lower part thereof and extending perpendicular to the longitudinal central plane of the cannula, the opposite ends of the two arms carrying the needles, and the piston ensures simultaneous pivoting of the two arms when it is displaced downward or upward, so that the needles emerge from or are drawn back into the cannula by the intermediary of two rocker arms, which on the one hand are linked to one another at the lower end of the piston rod by a joint pin integral with the piston parallel to the pivot pin of the support arms of the needles, and on the other hand are linked at their opposite ends in articulated manner respectively to the two support arms, in the vicinity of the needles.

The means for locking the rod in its collapsed position of the support member comprises two diametrically opposite lugs, which are integral with the upper part of the rod and project radially therefrom, and which are braced underneath or on top of the transverse sealing wall of the cannula depending on whether the support member is constituted by the flexible strip or by the two pivoting arms, this wall being provided with an oblong hole, which is defined on both sides of the central orifice for passage of the rod and which permits passage of the two lugs therethrough by rotation of the upper part of the rod relative to its lower part to release the rod and displace it axially in the cannula.

The invention also provides a procedure for closing, by subcutaneous suturing, an orifice made in the abdominal wall of a patient for passage of a trocar that has been used for a surgical operation by laparoscopy, using the instrument such as defined hereinabove, the said procedure being characterized in that it comprises introducing the cannula into the orifice immediately after extraction of the trocar while the abdomen is still inflated by a gas; displacing the piston relative to the cannula in a direction that makes it possible to act on the support member of the needles in such a way that the needles emerge through the slots of the lateral wall of the cannula underneath the abdominal wall; exerting a pulling movement on the cannula to introduce the needles into a thick part of the abdominal wall; displacing the piston in the cannula once again in opposite direction to cause the needles to pass through the entire thick part of the abdominal wall and the orifice and to be drawn back into the cannula through slots thereof and of the extraction means; displacing the extraction means relative to the cannula at the upper part thereof in such a way that the lower V-shaped rims of the slots of this means catch respectively the hook-shaped ends of the needles to retract them from the support member and introduce them into the cannula; pushing the cannula slightly back down into the orifice; operating the piston once again in the direction that makes it possible to retract the support member without the needles into the cannula; and withdrawing the cannula from the orifice to grasp and cut the two ends of the suture thread and to complete closing of the orifice.

The procedure also comprises, when the support member is constituted by the flexible strip, displacing the piston upward relative to the cannula, so that the needles emerge from the cannula, and displacing it toward the bottom of the cannula so that the needles are drawn partly back into the cannula and so that ultimately the strip is drawn completely back into the cannula before retraction thereof from the orifice.

As an alternative, the procedure also comprises, when the support member is constituted by the two articulated arms, displacing the piston downward relative to the cannula, so that the needles emerge from the cannula, and displacing it toward the top of the cannula, so that the needles are drawn partly back into the cannula and so that ultimately the arms are drawn completely back into the cannula before retraction thereof from the orifice.

Finally, the procedure comprises, after retraction of the cannula from the orifice, pulling on the free ends of the suture thread to tighten its loop underneath the abdominal wall and to ensure that the orifice can then be closed by knotting the cut ends of the thread.

The invention will be better understood, and other objectives, characteristics, details and advantages thereof will be made clearer in the explanatory description given hereinafter with reference to the attached schematic drawings, which are given only by way of example to illustrate two embodiments of the invention, and wherein:

DETAILED DESCRIPTION

Referring now to FIGS. 1 to 8, the inventive instrument is intended to permit closing, by subcutaneous suturing, of an orifice 1 made through an abdominal wall 2 of a patient for passage of a trocar that had been used beforehand for a surgical operation by laparoscopy.

Figure 1:
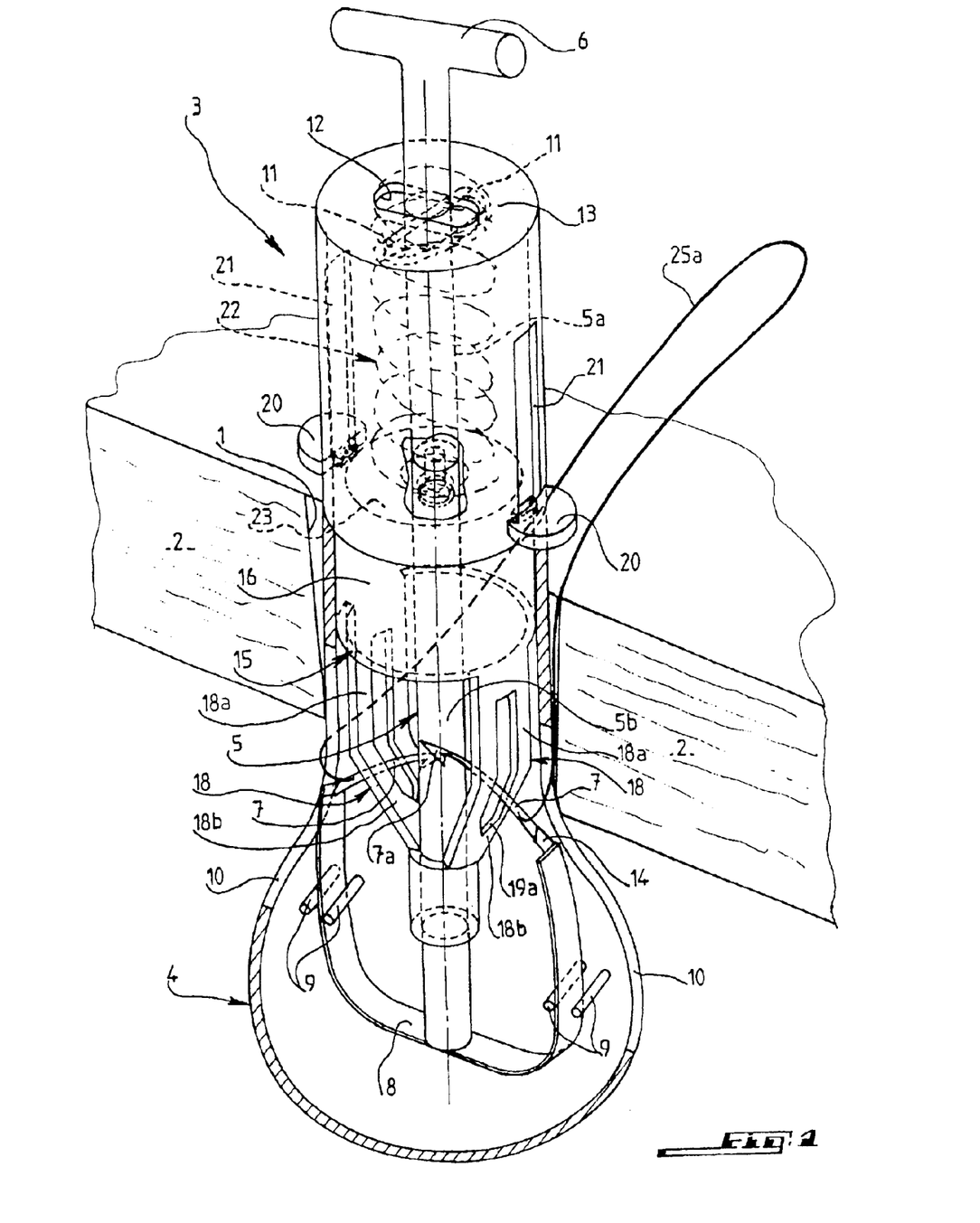
FIG. 1 is an exploded perspective view of the inventive instrument introduced through an abdominal wall of a patient.

The instrument comprises a cylindrical rigid cannula 3, of metal, for example, that can be partly introduced into orifice 1 immediately after retraction of the trocar once the surgical operation has been completed, or in other words at a time when the patient's abdomen is still inflated by an appropriate gas.

FIG. 1 illustrates the instrument in its initial position of introduction through orifice 1 of abdominal wall 2, where lower end part 4 of the instrument is situated in the abdomen underneath wall 2.

The instrument further comprises a central piston 5 in the form of a cylindrical rigid rod, which extends coaxially in cannula 3 and which can be operated manually from outside cannula 3 by the intermediary of an external handle 6 to slide axially in guided manner relative to cannula 3, as will be seen hereinafter.

The instrument further comprises two needles 7 attached movably to diametrically opposite ends of a support member 8 in the form of a flexible strip supported in lower end part 4 of cannula 3. To this end, flexible strip 8, by means of two pairs of support pins 9 parallel to strip 8 and disposed on both sides of the transverse central plane of this strip, symmetrically with respect to this plane, is maintained in part 4 such that it is perpendicular to the longitudinal central plane of cannula 3. Support pins 9, which are integral with the body of lower part 4 of cannula 3, are perpendicular to the longitudinal central plane of the cannula, and the two pins 9 of each pair are situated on each side of strip 8 in immediate proximity thereto, while being offset relative to one another along strip 8.

Figure 2:
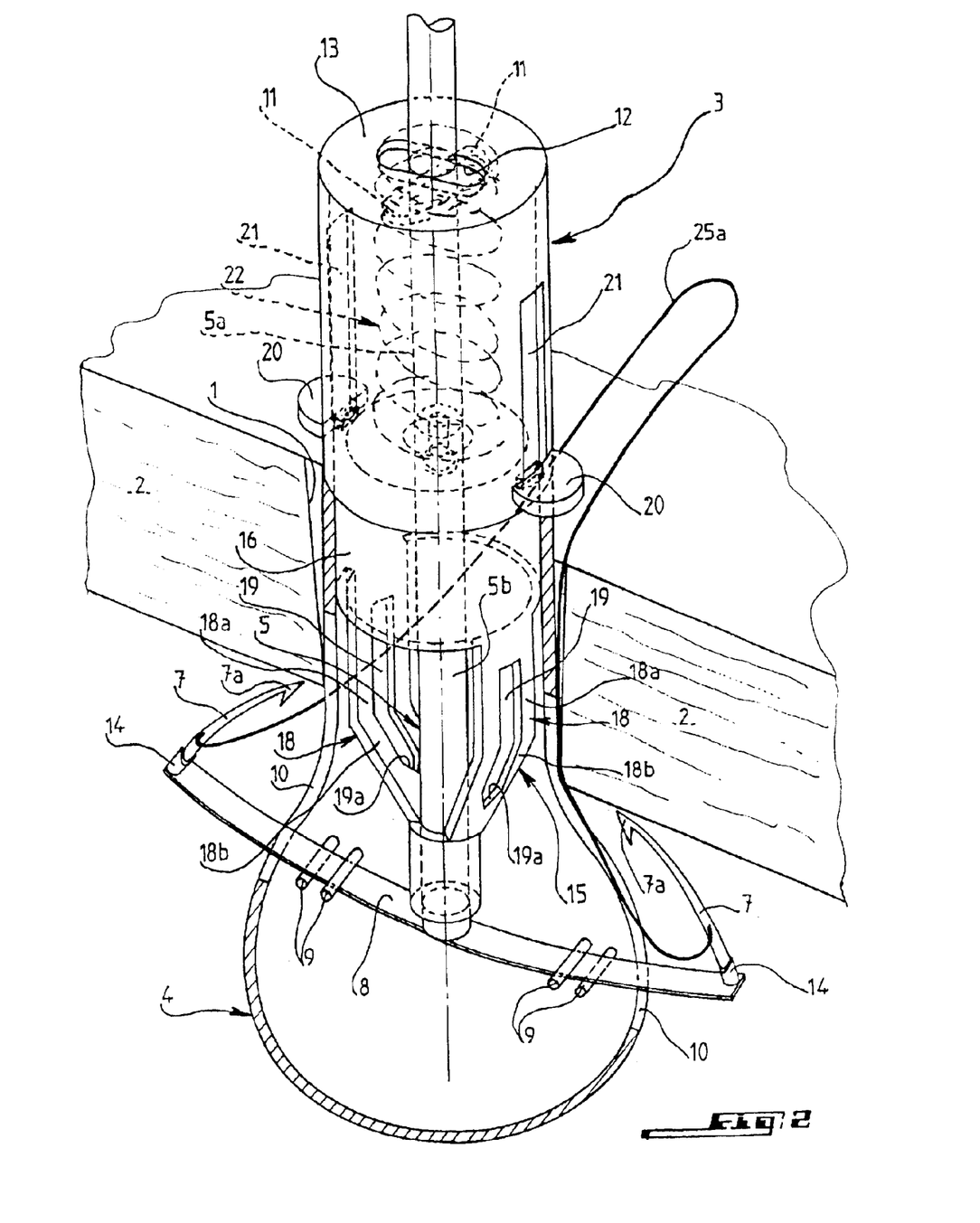
FIGS. 2 to 8 illustrate the instrument of FIG. 1 in different phases of functioning for closing, by subcutaneous suturing, an orifice made in the abdominal wall of the patient.
Figure 7:
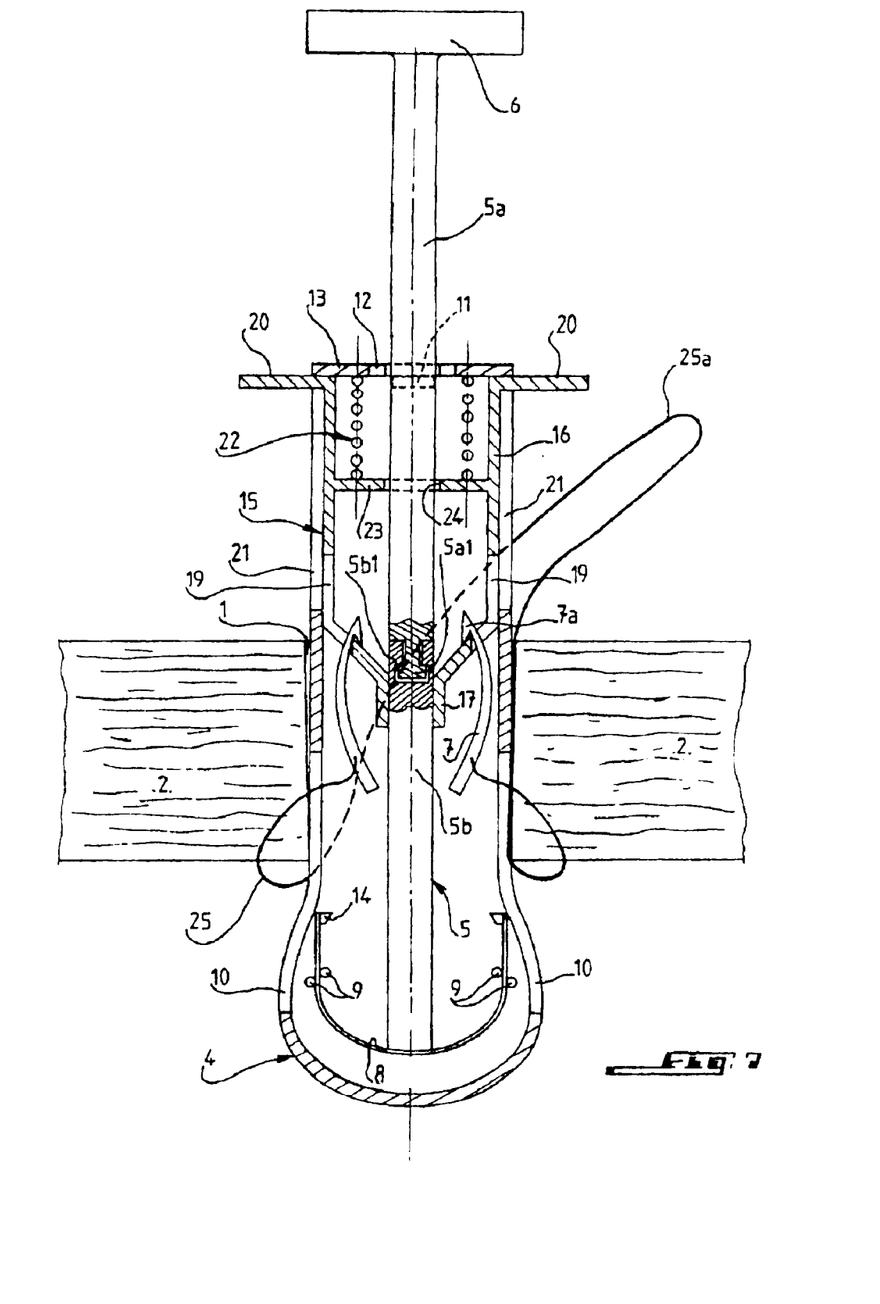

The lower end of piston rod 5 is integral, by any appropriate means such as a fastening screw, with the geometric center of support strip 8 in such a way that displacement of rod 5 toward the top of cannula 3 causes elastic deformation of strip 8, such that it slides between the pairs of support pins 9, while the opposite end parts of strip 8 emerge through respectively two diametrically opposite longitudinal rectangular slots 10 made through the lateral wall of the body of lower end part 4 of cannula 3, in such a way that the two needles 7 project completely outside end part 4, as illustrated in FIG. 2. Displacement of piston rod 5 downward from its position illustrated in FIG. 2 causes strip 8 to bend by deformation toward the lower end of cannula 3, and also causes strip 8 to slide between the two pairs of support pins 9, which deform strip 8 in such a way that its end parts can again enter end part 4 of cannula 3 through the two slots 10, as illustrated in FIG. 7.

Piston rod 5 is locked in its initial position illustrated in FIG. 1 by a manually releasable locking means constituted by two lugs 11 integral with rod 5 in upper part 5a thereof and projecting therefrom in diametrically opposite positions. The two lugs 11 can occupy a crosswise position relative to an oblong hole 12 cut through circular sealing wall 13 of the upper end of cannula 3, the two lugs 11 being braced against the underside of the said wall under the action of the elastic reaction force exerted by strip 8 on rod 5. By means of handle 6, upper part 5a of rod 5 can be turned by about 90° relative to lower part 5b thereof to bring the two lugs 11 into vertical alignment with oblong hole 12, in order to release rod 5 from cannula 3 and to permit a pulling force to be exerted on rod 5 to cause displacement of strip 8 in a direction that allows needles 7 to emerge from end part 4 through the two slots 10. As is evident in particular from FIG. 4, upper part 5a of rod 5 is provided at its end with a circular head 5a1 of smaller diameter engaged in a countersunk cavity 5b1 of conjugate shape made at the end of lower part 5b of rod 5 opposite from strip 8, in such a way as to permit rotation of upper part 5a relative to lower part 5b of rod 5. Head 5a1 can be constituted by the head of a screw, whose threaded part is immobilized by being screwed into the lower end of part 5a of rod 5, coaxially therewith.

Needles 7 are each mounted at the corresponding end of strip 8 in a base 14, which is integral with the end of strip 8 and has a cross section that can be circular, triangular or other. The axis of each base 14 is inclined relative to the corresponding end support plane of strip 8 in order to facilitate extraction of needle 7, as will be seen hereinafter. As an alternative, also to facilitate extraction of each needle 7, each base 14 can have its axis perpendicular to the corresponding end plane of strip 8 but can be provided with a free end face inclined relative to this end plane in such a way that the end of needle 7 engaging in base 14 has a shoulder part bearing against this inclined face.

Needles 7, which are identical, curved and directed toward one another, are situated respectively in two planes parallel to the longitudinal central plane of cannula 3 and disposed on both sides of this plane at substantially equal distances therefrom, these two parallel planes also being situated on both sides of piston rod 5 in such a way as to permit needles 7 to occupy their initial drawn-in position, in which they cross one another in end part 4 of cannula 3. In FIG. 2, needles 7 are situated above strip 8. Each needle 7 is terminated by a hook-shaped pointed part 7a.

Figure 8:
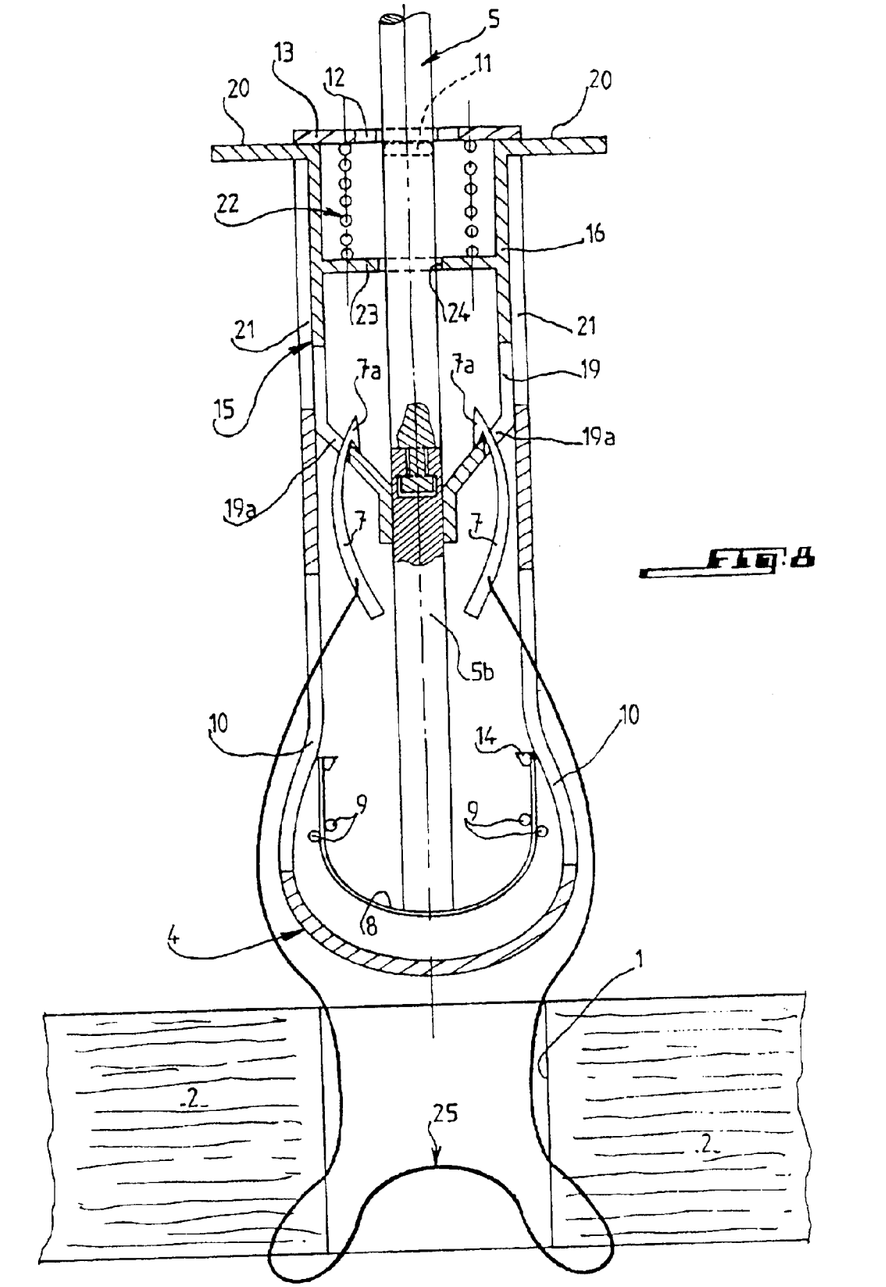

The instrument also comprises, for extraction of needles 7, a means 15, which is mounted slidingly in cannula 3, concentrically with rod 5, and which can be maneuvered from the outside in order to displace it from a low position in end part 4 of cannula 3, as illustrated in FIGS. 1 to 4, to a high position in the upper part of cannula 3, as illustrated in FIG. 8, in such a way that, during this displacement, it simultaneously catches the two needles 7 introduced beforehand into abdominal wall 2 by penetrating obliquely toward one another in orifice 1 and cannula 3 through longitudinal slots 10, and it extracts needles 7 from flexible strip 8 in order to guide them upward into cannula 3.

Thus extraction means 15 comprises a cylindrical upper part 16 that can slide along the corresponding internal lateral surface of cannula 3, a cylindrical lower end part 17 of smaller diameter, in which there is slidingly mounted lower part 5b of rod 5, and an intermediate linking part constituted by two opposite walls 18 situated on both sides of rod 5, each wall 18 being provided with a straight part 18a parallel to rod 5 and an oblique part 18b converging toward lower end part 17. Each wall 18 is provided with a longitudinal slot 19 that permits the passage of corresponding needle 7 and that is terminated above lower part 17 of extraction means 15 by two V-shaped rims 19a, at the bottom of which there can be caught hook-shaped end 7a of needle 7 during displacement of extraction means 15 toward the top of cannula 3. By the fact that needles 7 are offset from the longitudinal central plane of cannula 3, slots 19 are also so offset.

To permit rotation of upper part 5a of rod 5 relative to its lower part 5b during the operation of release of rod 5 from cannula 3 starting from its initial position illustrated in FIG. 1, lower part 5b can be grooved to engage slidingly in the corresponding grooved bore of lower part 17 of extraction means 15. This arrangement is not imperative, however, because the assembly constituted by the end of rod 5, strip 8 and pins 9 maintains lower part 5b of rod 5 in rotational relationship with the cannula.

Extraction means 15 is further provided with two diametrically opposite external gripping tabs 20, which are integral with cylindrical upper part 16, project radially through two longitudinal slots 21 respectively of the lateral wall of cannula 3, and are situated above slots 10 for passage of needles 7.

Extraction means 15 is pushed back toward its low position in cannula 3 by a precompressed helical pressure spring 22 mounted between upper sealing wall 13 of cannula 3 and an internal transverse wall 23 of extraction means 15, situated in cylindrical upper part 16 thereof. Wall 23 has a circular central orifice 24 through which rod 5 passes.

A suture thread 25, whose two free ends are integral with the two needles 7 respectively at the ends opposite their hook-shaped ends 7a, has sufficient length to form a loop 25a which, from the moment that the instrument is introduced into abdominal wall 2, is situated outside thereof and is maintained outside until retraction of the instrument from wall 2. Each end 7 of thread 25 can be fixed to corresponding metal needle 7 by crimping.

To ensure that it is a traumatic, lower part 4 of cannula 3 has a bulb-like end in which there are disposed support pins 9 of strip 8.

The functioning of the instrument follows already from the description given hereinabove, and will now be explained.

Under the initial conditions of use of the instrument, extraction means 15 occupies its low position in cannula 3 under the action of return spring 22 and the two tabs 20, braced respectively against the two lower rims of the two slots 21 of cannula 3, and rod 15 is locked in its lowest position in cannula 3, thus exerting on strip 8 a pressure that maintains the ends of strip 8 and of the two needles 7 inside end part 4 of cannula 3, as illustrated in FIG. 1.

The instrument is then introduced into orifice 1 through wall 2, until lower end part 4 is situated in the abdomen underneath wall 2. This maneuver is performed immediately after extraction of the trocar used beforehand for the surgical operation by laparoscopy, while the abdomen is kept inflated by the gas to prevent injury to the internal organs. During introduction of the instrument through abdominal wall 2, the surgeon will have been careful to keep loop 25a of thread 25 outside the patient's body, while the end parts of the thread pass into orifice 1 and respectively through the two slots 10 of end part 4.

Rod 5 is then released from cannula 3 by turning upper part 5a by means of handle 6 until the two lugs 11 become vertically aligned with oblong hole 12, after which the surgeon exerts a pulling force on rod 5, thus displacing the geometric center of strip 8 toward the top of cannula 3 and, by the fact that this slides between the two pairs of support pins 9, making the two ends of strip 8 and the two needles 7 tilt apart from one another as far as the position illustrated in FIG. 2, where the two needles 7 are disposed just underneath the internal face of abdominal wall 2. Thus the two needles 7 are displaced in their respective parallel planes from their crossed position on both sides of rod 5 as illustrated in FIG. 1 to their position illustrated in FIG. 2, by passing through slots 19 of extraction means 15 and slots 10 of end part 4 of cannula 3.

Figure 3:
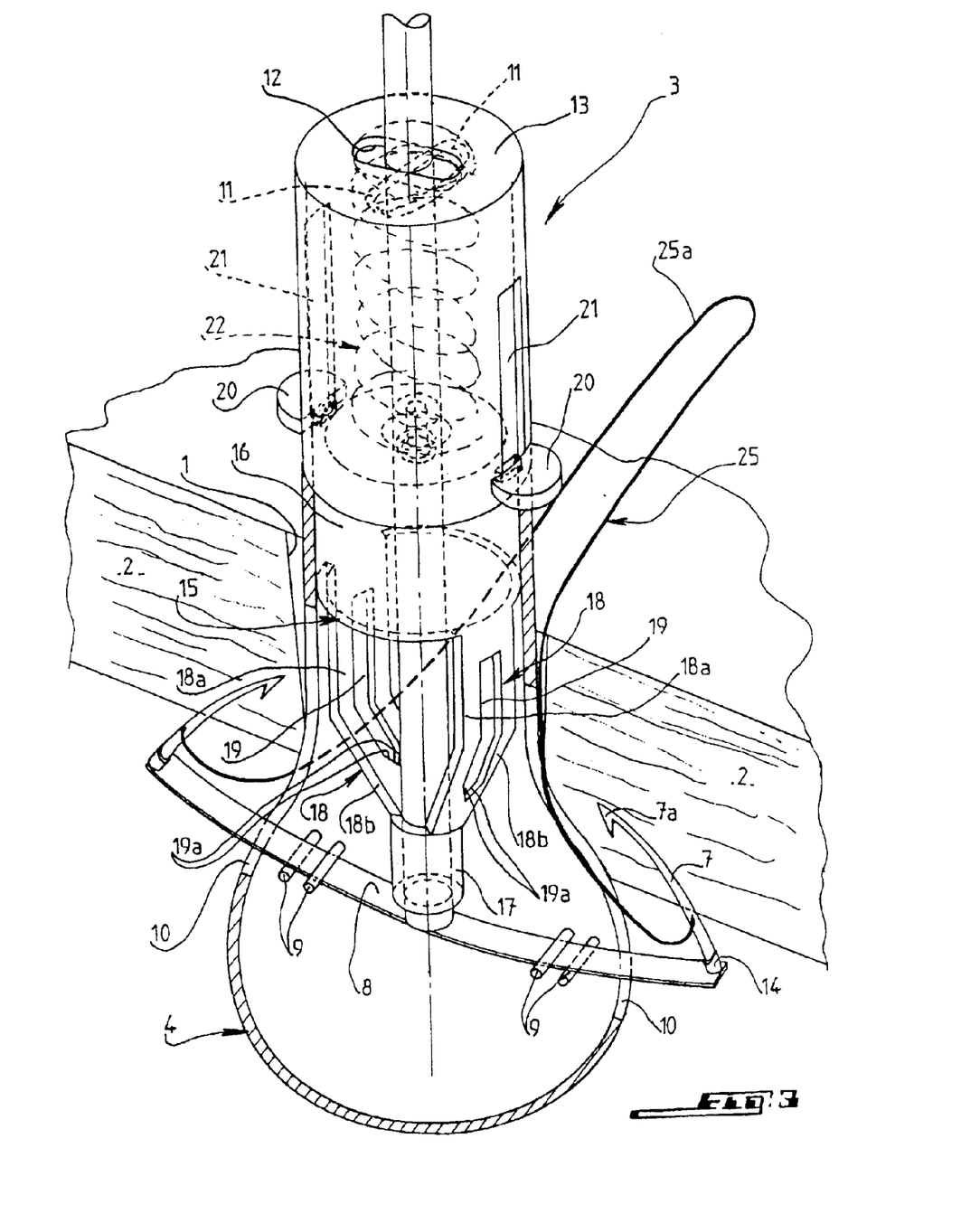

Starting from the position illustrated in FIG. 2, the surgeon exerts on the instrument an upward pulling force to introduce needles 7 into a thick part of the aponeurosis of abdominal wall 2, as illustrated in FIG. 3.

Figure 4:
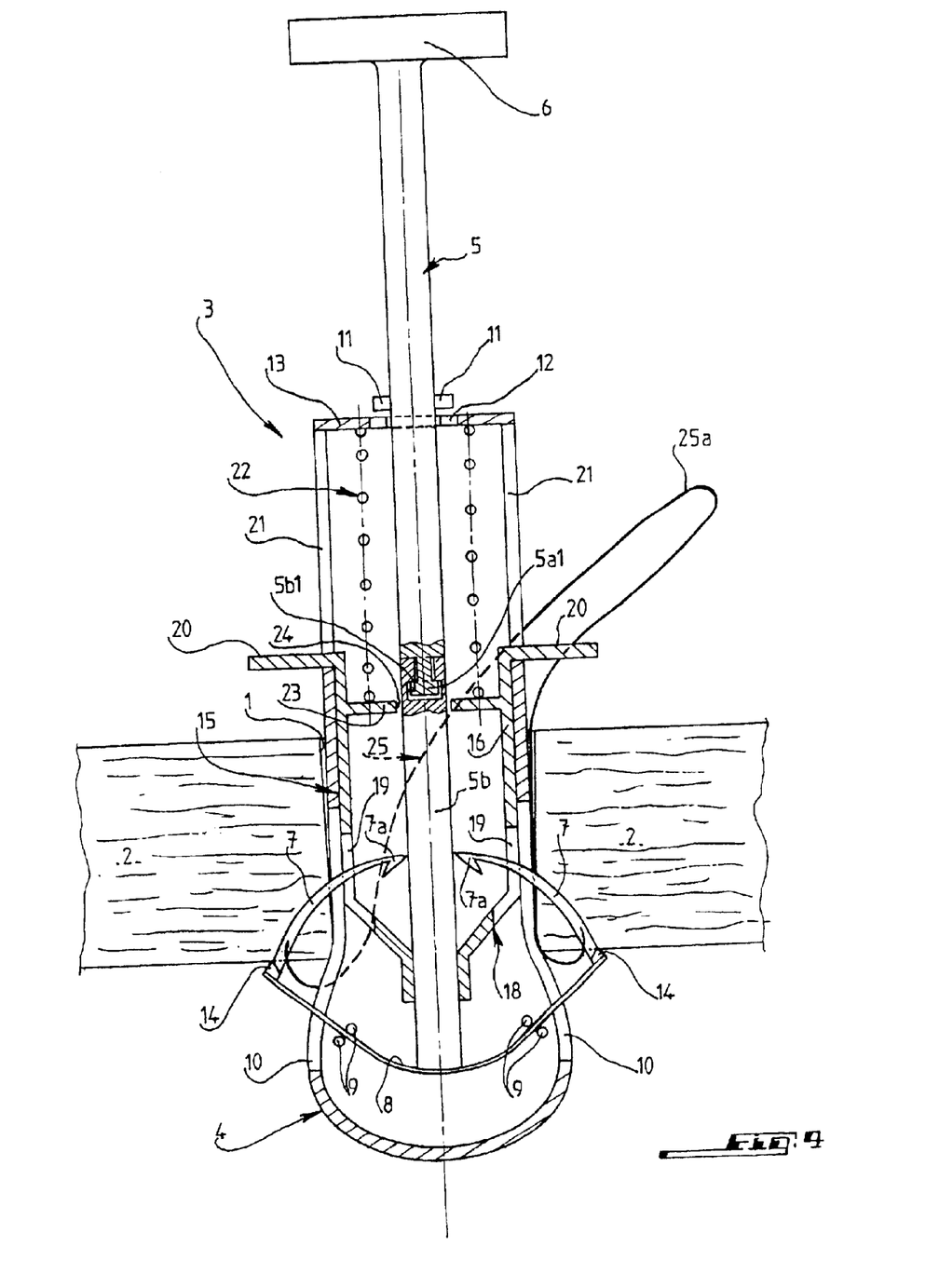

The surgeon then pushes rod 5 back down into cannula 3, with the result that the lower end of rod 5 causes strip 8 to fold by bending and to slide between the two pairs of pins 9, so that needles 7 pass completely through the thick part of abdominal wall 2 and become engaged in cannula 3 through slots 10 of end part 4 of cannula 3 and slots 19 of extraction means 15, as illustrated in FIG. 4.

Figure 5:
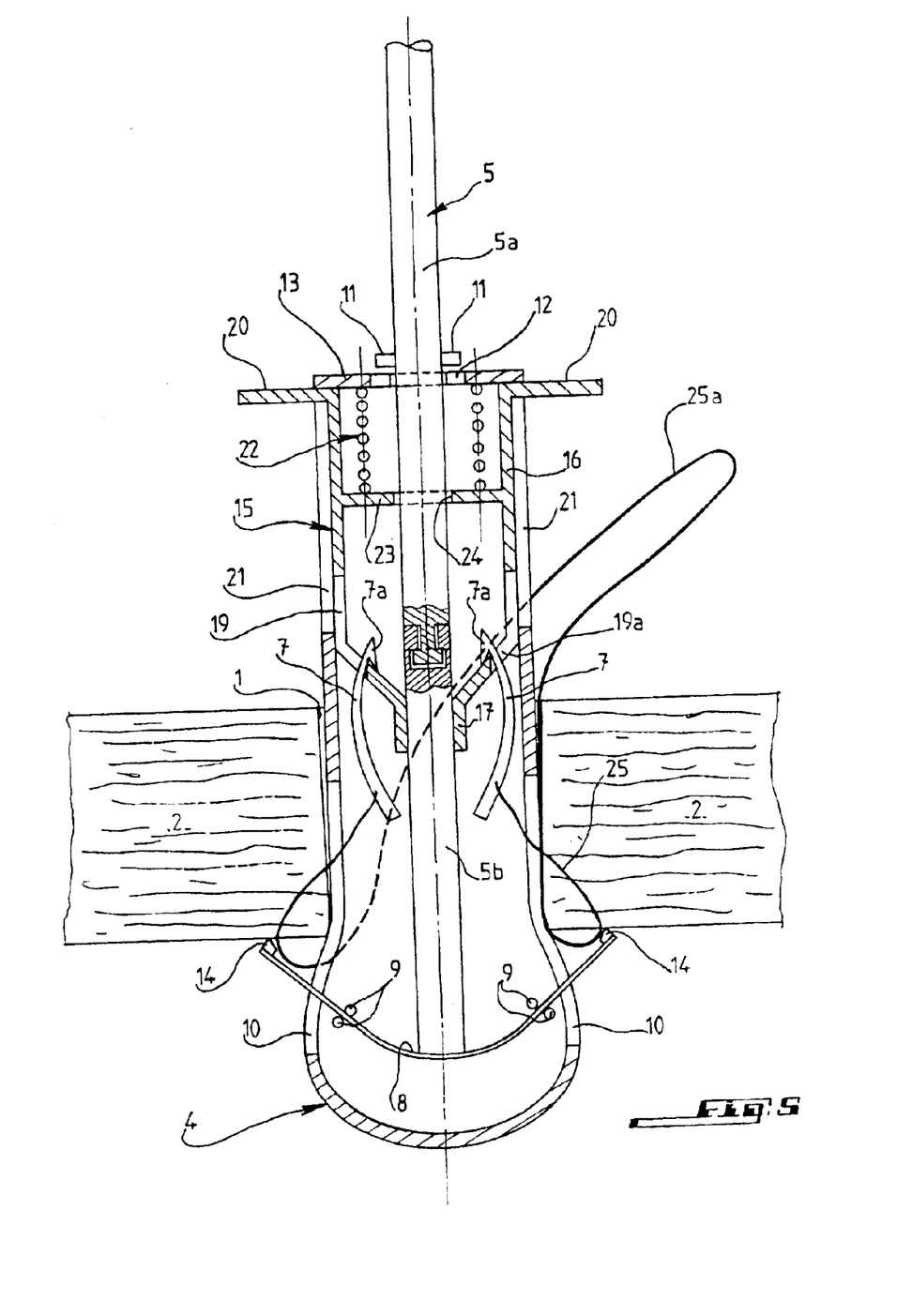
Figure 6:
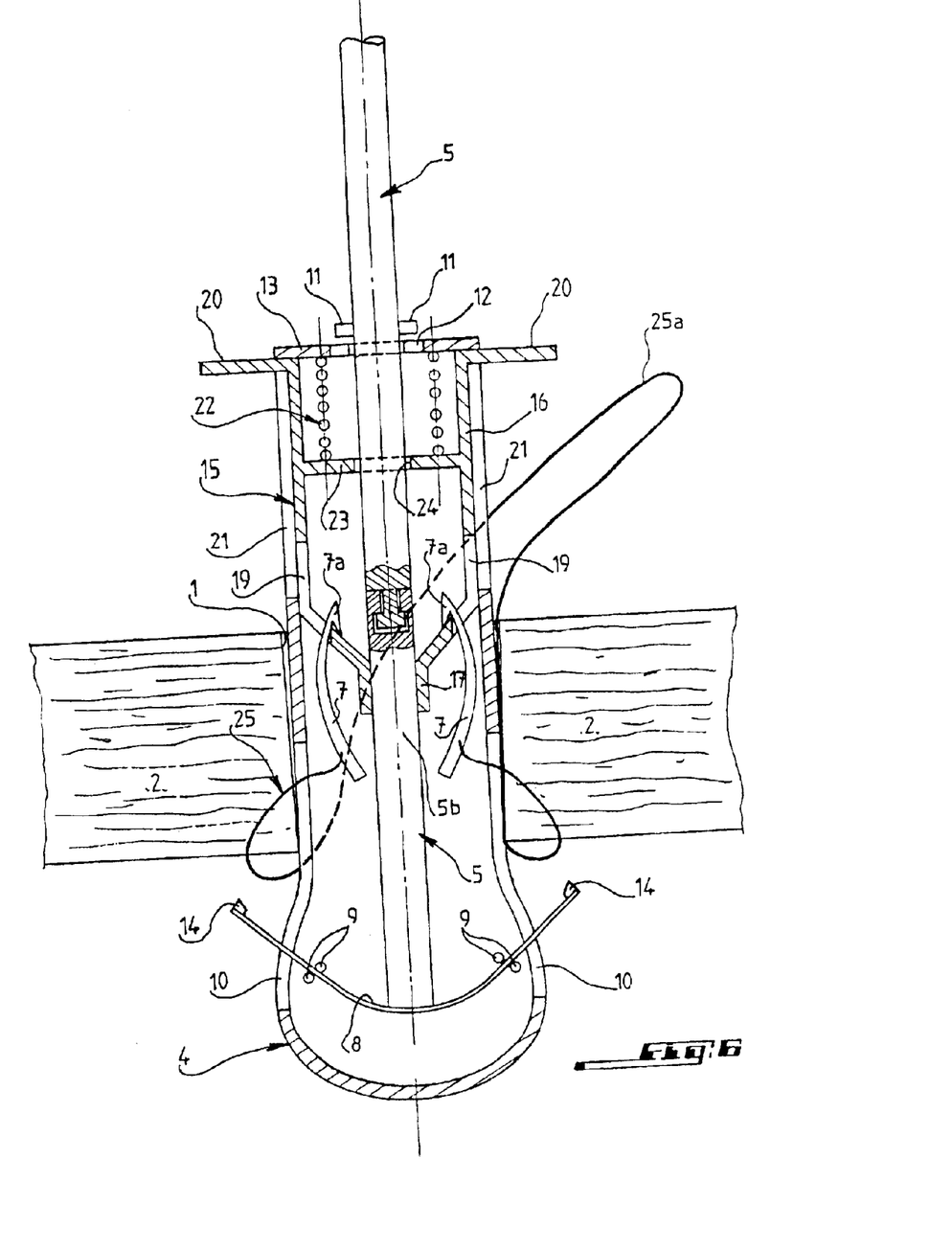

Using the two external tabs 20, the surgeon then displaces extraction means 15 toward the top of cannula 3 until tabs 20 are stopped against the respective upper rims of the two slots 21 of cannula 3 as illustrated in FIG. 5. This figure shows that, during the upward displacement of extraction means 15, the V-shaped lower rims of the two slots 19 have caught hook-shaped ends 7a of needles 7, thus disengaging them from their respective bases 14, so that the end parts of thread 25 are pulled by the needles into cannula 3 through the two slots 10. FIG. 5 also shows that the two bases 14 are disposed practically just underneath abdominal wall 2.

The surgeon then pushes the instrument in order to position lower end part 4 of the cannula at a certain distance from abdominal wall 2 (FIG. 6) and to ensure, by thrust exerted on piston rod 5, that flexible strip 8 becomes folded once again to the extent that its end parts, now without the needles, are once again draw into end part 4, as illustrated in FIG. 7. The surgeon maneuvers handle 6 to make upper part 5a of rod 5 turn relative to its lower part 5b and to bring the two lugs 11 into locking position of rod 5 underneath the upper sealing wall of cannula 3.

Finally, the instrument is completely withdrawn from orifice 1 as illustrated in FIG. 8, and thread 25, which is integral with needles 7, is pulled in such a way that it continues to pass through the thickness of abdominal wall 2 along the same path as needles 7 until loop 25a is situated substantially at the bottom of orifice 1 at the level of the internal face of abdominal wall 2. All that is then left for the surgeon is to cut the two end parts of thread 25 and to tie a knot manually with the two strands of the thread, ensuring that the part of the thread loop underneath wall 2 is taut, in order to pull together and close the facing walls of orifice 1 comprising the aponeurosis and the deep muscle layer.

Figure 9:
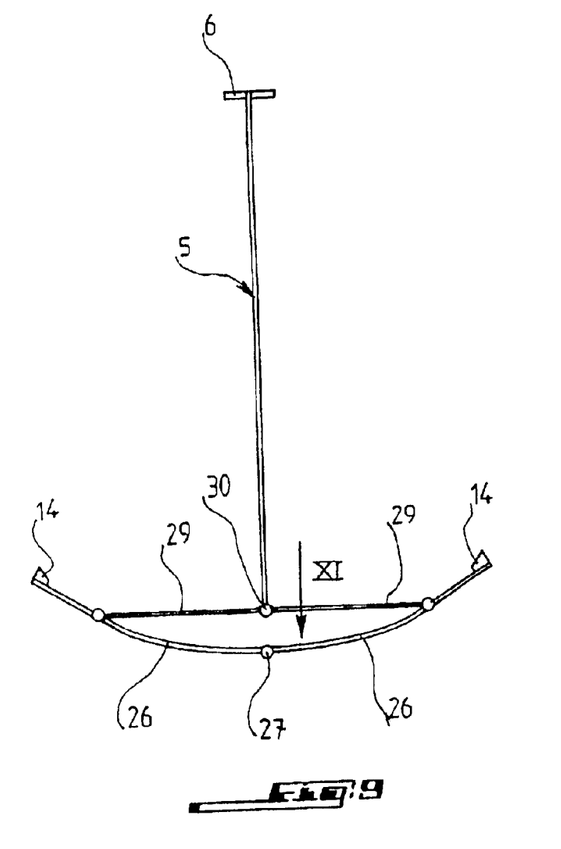
FIG. 9 illustrates another embodiment, shown in its extended position, of the needle-support member comprising part of the orifice-closing instrument.
Figure 10:
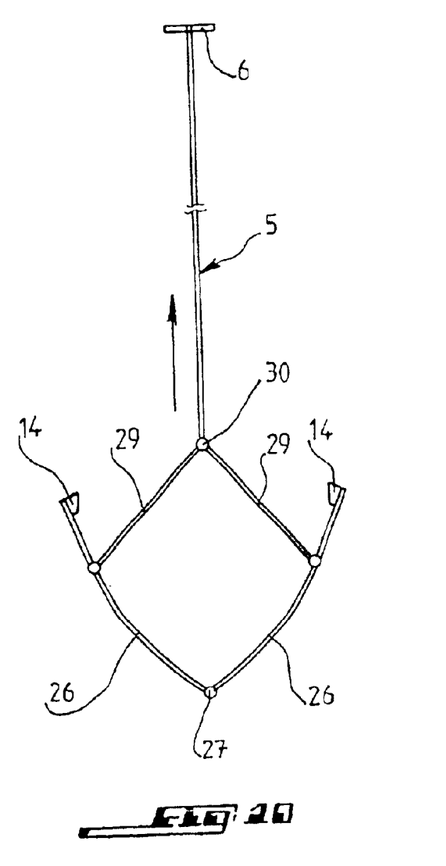
FIG. 10 is a view of the support member of FIG. 9 in collapsed position.
Figure 11:
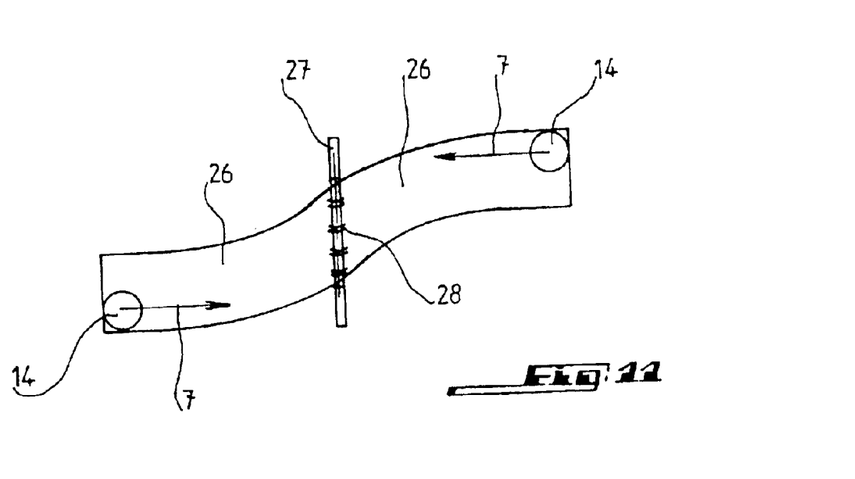
FIG. 11 is an overhead view in the direction of arrow XI of FIG. 9.

FIGS. 9 to 11 illustrate another embodiment of the support member for needles 7, for use as an alternative to that constituted by flexible strip 8 of the first embodiment.

According to this second embodiment, the support member is constituted by two arms 26 mounted pivotally on a common central pin 27 integral with the body of the cannula in lower part 4 thereof and extending perpendicular to the longitudinal central plane of the cannula. Pin 27 can be fixed by its ends, which are force-fitted respectively in two opposite coaxial holes drilled in the lateral wall of end part 4 of cannula 3, and the two arms 26 are mounted pivotally on pin 27 in the manner of a swinging hinge 28.

The two arms 26 are provided with the two bases 14, which are integral with their opposite ends and in which the two needles 7 are movably mounted. To permit the two bases 14 to be situated in two planes which are spaced apart and parallel to the longitudinal central plane of cannula 3, the two arms 26, as seen from above, have an elongated S-shaped configuration, whose incurvate branches are situated on both sides of pin 27, the two bases being situated on a diagonal passing through the geometric center of pin 27.

Piston rod 5, which is identical to rod 5 of the first embodiment, ensures simultaneous pivoting of the two arms 26 by the intermediary of two rocker arms 29, which on the one hand are linked to one another at the lower end of rod 5 by a joint pin 30 integral with the rod and parallel to pivot pin 27, and on the other hand are linked at their opposite ends in articulated manner respectively to the two support arms 26, in the vicinity of support bases 14 of needles 7.

When the instrument is introduced through abdominal wall 2, the two arms 26 occupy their position illustrated in FIG. 10, where the two arms are raised above joint pin 27 in a manner defining an acute angle in which the end parts of arms 26 and their associated needles 7 are lodged in lower end part 4 of cannula 3.

To extend the two arms 26 to their open position projecting through slots 10 of lower part 4 of cannula 3, the surgeon exerts a thrust on piston rod 5 toward the bottom of the cannula, such that the two rocker arms 29 make the two arms 26 pivot around pin 27, thus spreading them apart as far as the position in which needles 7 are disposed underneath wall 2, as illustrated in FIG. 2.

Otherwise the functioning principle of the instrument equipped with the support member according to the second embodiment is identical to that described previously with reference to the first embodiment, with the exceptions that a pushing force must be exerted on piston 5 to extend the needles to their position in which they project outside cannula 3 and that rod 5 must be pulled to fold the two arms 26 once again such that they approach one another and become lodged, without the needles, in end part 4 of cannula 3 before complete extraction of the instrument from orifice 1. The other difference that exists relative to the first embodiment is that locking of rod 5, especially in the position in which arms 26 and needles 7 are lodged in end part 4 before introduction of the cannula into wall 2, is achieved by positioning the two locking lugs 11 against the upper sealing wall of cannula 3 crosswise relative to oblong hole 12 and, to facilitate extension of the two arms 26 to their position illustrated in FIG. 9, it is possible to provide a torsion spring wound around pivot pin 27 and exerting on the two arms 26 an elastic force tending to spread them apart and maintain them in their extended position.

The instrument according to the invention makes it possible efficiently to close the orifice for passage of the trocar and to suture the muscle and aponeurosis of the abdominal wall of a patient.

By way of indication, the instrument can have a length of about 20 cm with a maximum outside diameter of 12 mm at the level of its bulb-like part, while the diameter of the cannula over two thirds of its length can be 10 mm. In projecting position of flexible strip 8 or of support arms 26 of needles 7, their ends can extend beyond lower end part 4 of cannula 3 by 5 to 7 mm on both sides thereof. Of course, these dimensions are given by way of non-limitative example.

What is claimed is:

1. An instrument for closing, by subcutaneous suturing, an orifice (1) made in the abdominal wall (2) of a patient for passage of a trocar that has been used for a surgical operation by laparoscopy, characterized in that it comprises a cylindrical rigid cannula (3), one end part (4) of which can be introduced into the orifice (1); a piston (5) extending coaxially in the cannula (3) and being operable externally by an operator; two needles (7) movably attached to the diametrically opposite ends of a support member (8; 26), which itself is supported in the end part (4) of the cannula (3) and which can occupy, under the action of the piston (5), a collapsed position in which the needles (7) are drawn back into the end part (4) of the cannula and an extended position after introduction of the cannula (3) into the orifice (1), in which case the needles (7) project completely out of the cannula underneath the abdominal wall (2) by passing through respectively two longitudinal slots (10) of the lateral wall of the cannula (3), and are inclined relative to the longitudinal axis of the cannula (3) on both sides thereof and are directed toward one another; a means (15) for extracting the needles (7), which is mounted slidingly in the cannula (3), concentrically with the piston (5), and which can be maneuvered by the operator so that it can be displaced from a low position in the end part (4) of the cannula (3) to a high position in the upper end part thereof in such a way that, during this displacement, it simultaneously catches the two needles (7), which were introduced beforehand into the abdominal wall (2) and which penetrate obliquely toward one another in the orifice (1) and the cannula (3) through longitudinal slots (10), and extracts them from the support member (8; 26) in order to guide them into the cannula (3), at the same time pulling a suture thread (25) into the abdominal wall (2) and the cannula (3), the thread (25) having its ends integral respectively with the two needles (7) and defining a loop (25a), which is situated outside the cannula and which passes through the orifice (1) to the outside of the abdominal wall (2), the ends of the thread (25) then being accessible, so that they can be grasped and cut by the operator after complete retraction of the cannula (3) from the orifice (1), in order to close the said orifice by tying a knot with the two strands of the thread (25).

2. An instrument according to claim 1, characterized in that the piston is a central rigid rod (5), which is guided slidingly in the extraction means (15) and whose lower end is connected to the support member (8; 26) of the needles (7) and whose upper end part (5a) passes through an upper transverse sealing wall (13) of the cannula (3), the rod (5) capable of being retained axially in the cannula (3) by a manually releasable locking means (11) in such a way as to exert on the support member (8; 26) an axial force for retracting the needles (7) into the cannula (3) to permit introduction thereof into the orifice (1), after which the operator can release the locking means (11) to displace the rod (5) in a direction that causes extension of the support member (8; 26) and emergence of the needles (7) from the cannula (3).

3. An instrument according to claim 2, characterized in that the extraction means (15) comprises a sliding cylindrical upper part (16) in the cannula (3), a cylindrical lower end part (17) of smaller diameter, in which there is slidingly mounted the lower end part (5b) of the rod (5), and an intermediate linking part constituted in particular by two oblique walls (18b), which converge toward the lower end part (17) and each of which comprises a longitudinal slot (19) that permits, when the extraction means (15) is in low position, passage of the corresponding needle (7) to its emerged position, in which it projects out of the cannula (3), each slot (19) being terminated above the lower part (17) of the extraction means (15) by two V-shaped rims (19a), in which the hook-shaped end (7a) of the needle (7) can be caught during the displacement of the extraction means (15) toward the upper part of the cannula (3).

4. An instrument according to claim 3, characterized in that the extraction means (15) comprises two diametrically opposite external gripping tabs (20), which are integral with the upper part (16) of this means and project radially through respectively two longitudinal slots (21) situated in the lateral wall of the cannula (3) at positions above the slots (10) for passage of the needles (7), and in that a precompressed spring (22) is mounted between the extraction means (15) and the cannula (3) to return the extraction means (15) to its low position.

5. An instrument according to claim 2, wherein the support member comprises a flexible strip (8) having ends carrying the two needles (7), said instrument comprising means for maintaining the strip in the lower end part (4) of the cannula (3) such that it is perpendicular to a longitudinal middle plane thereof, said means for maintaining comprising two pairs of support pins (9) which are parallel to the strip (8), disposed on both sides of the transverse central plane of the strip (8) symmetrically with respect thereto, and integral with the body of the cannula (3) and perpendicular to its longitudinal central plane, the two pins (9) of each pair being disposed on each side of the strip (8) in immediate proximity thereto so as to allow modification, by bending, of a radius of curvature of the strip (8) by sliding the strip between the support pins (9) under the action of the piston rod (5), the piston rod having a lower end that is integral with a geometric center of the strip (8) so that the piston rod can displace the geometric center of the strip toward the top or toward the bottom of the cannula (3) to cause, the needles (7) to emerge from or to be drawn back into the cannula (3).

6. An instrument according to claim 5, wherein the locking means comprises two diametrically opposite lugs (11), which are integral with the upper end part (5a) of the rod (5) and project radially therefrom, and which are braced underneath or on top of the transverse sealing wall (13) of the cannula (3), the wall (13) being provided with an oblong hole (12), which is defined on both sides of the central orifice for passage of the rod (5) and which permits passage of the two lugs (11) therethrough by rotation of the upper end part (5a) of the rod (5) relative to a lower end part (5b) to release the rod (5) and displace it axially in the cannula (3).

7. An instrument according to claim 2, wherein the support member comprises two support arms (26) mounted pivotally on a common central pin (27) integral with the body of the cannula (3) in the lower end part (4) thereof and extending perpendicular to a longitudinal central plane of the cannula, the two support arms (26) comprising opposite ends carrying the needles (7), and wherein the piston (5) causes simultaneous pivoting of the two support arms (26) when the piston is displaced downward or upward which in turn causes the needles (7) to emerge from or to be drawn back into the cannula (3) by the intermediary of two rocker arms (29), said rocker arms being linked to one another at a lower end of the piston rod (5) by a joint pin (30) integral with the piston and parallel to the central pin (27) of the support arms (26), said rocker arms also being linked at opposite ends in articulated manner respectively to the two support arms (26), in the vicinity of the needles (7).

8. An instrument according to claim 1, wherein the needles (7) are curved and situated respectively in two planes which are parallel to a longitudinal central plane of the cannula (3) and are disposed on both sides of the longitudinal central plane of the cannula at equal distances therefrom so as to allow the needles (7) to occupy a drawn-in position in which they cross in the end part (4) of the cannula (3).

9. An instrument according to claim 8, wherein the two planes containing the two needles (7) are situated on both sides of the piston rod (5).

10. An instrument according to claim 1, wherein the needles (7) comprise hook-shaped ends (7a) and are mounted movably via ends of the needles at positions opposite to the hook-shaped ends (7a) respectively in two bases (14), said bases being integral with the ends of the support member (8; 26), each of the bases (14) being inclined relative to a corresponding end support plane of the support member to facilitate extraction of the needles (7) during upward movement of the extraction means (15) in the cannula (3).

11. An instrument according to claim 1, wherein the cannula is displaceable by pulling such that, when the needles (7) are in a position in which they have emerged from the cannula (3), the needles (7) can be made to penetrate into the abdominal wall (2), and wherein the piston (5) is operable in a direction that allows the needles (7) to be retracted toward the cannula (3) and the ends thereof to penetrate into the orifice (1) and into the cannula (3) through the two longitudinal slots (10) thereof.

12. A method for closing, by subcutaneous suturing, an orifice (1) made in the abdominal wall (2) of a patient for passage of a trocar that has been used for a surgical operation by laparoscopy, the method comprising: (a) providing the instrument of claim 1 and providing the needles with respective ends of a suture thread; (b) introducing the cannula (3) into the orifice (1) immediately after extraction of the trocar while the abdomen is still inflated by a gas; (c) displacing the piston (5) relative to the cannula (3) in a direction that makes it possible to act on the support member (8; 26) of the needles (7) in such a way that the needles emerge through the slots (10) of the lateral wall of the cannula (3) underneath the abdominal wall (2); (d) exerting a pulling movement on the cannula (3) to introduce the needles (7) into a thick part of the abdominal wall (2); (e) displacing the piston (5) in the cannula (3) once again in opposite direction to cause the needles (7) to pass through a thick part of the abdominal wall (2) and to be drawn back into the cannula (3) through slots (10; 19) of the extraction means (15); (f) displacing the extraction means (15) relative to the cannula (3) at an upper part thereof in such a way that the extraction means (15) catch respective of the needles (7) to retract them from the support member (8; 26) and introduce them into the cannula (3); (g) operating the piston (5) once again in a direction that makes it possible to retract the support member (8; 26) without the needles (7) into the cannula (3); and (h) withdrawing the cannula (3) from the orifice (1) to enable grasping of the ends of the suture thread (15) and to complete closing of the orifice (1).

13. The method according to claim 12, wherein the support member comprises a flexible strip (8), and the method comprises displacing the piston (5) upward relative to the cannula (3), so that the needles (7) emerge from the cannula (3), and displacing the piston toward the bottom of the cannula so that the needles (7) are drawn partly back into the cannula (3) and so that ultimately the strip (8) is drawn completely back into the cannula (3) before retraction of the cannula from the orifice (1).

14. The method according to claim 12, wherein the support member comprises two articulated arms (26), and the method comprises displacing the piston (5) downward relative to the cannula (3) so that the needles (7) emerge from the cannula, and displacing the piston toward the top of the cannula, so that the needles (7) are drawn partly back into the cannula and so that ultimately the arms (26) are drawn completely back into the cannula (3) before retraction of the cannula from the orifice (1).

15. The method according to claim 12, wherein after retraction of the cannula (3) from the orifice (1), the method further comprises pulling on free ends of the thread (15) to tighten its loop (15a) underneath the abdominal wall (2) and to ensure that the orifice (1) can then be closed by knotting cut ends of the thread (25).

* * * * *